United States Patent [19]
Inamoto et al.

[11] 3,948,966
[45] Apr. 6, 1976

[54] PROCESS FOR PREPARING BENZENE DERIVATIVES HAVING ISOCYANATOMETHYL GROUP

[75] Inventors: Yoshiaki Inamoto, Wakayama; Hisao Kitano; Yoshiaki Tanaka, both of Osaka; Fumio Tanimoto, Kyoto; Atsushi Nishibata; Susumu Handa, both of Wakayama, all of Japan

[73] Assignee: Kao Soap Co., Ltd., Tokyo, Japan

[22] Filed: Oct. 11, 1974

[21] Appl. No.: 514,100

[30] Foreign Application Priority Data
Oct. 18, 1973  Japan............................ 48-117181

[52] U.S. Cl............................................. 260/453 P
[51] Int. Cl.².................................. C07C 118/00
[58] Field of Search.............................. 260/453 P

[56] References Cited
UNITED STATES PATENTS

| | | | |
|---|---|---|---|
| 2,866,801 | 12/1958 | Himel et al. | 260/453 |
| 3,584,028 | 6/1971 | Argabright et al. | 260/453 |

*Primary Examiner*—Lewis Gotts
*Assistant Examiner*—Dolph H. Torrence
*Attorney, Agent, or Firm*—Woodhams, Blanchard and Flynn

[57] ABSTRACT

A process for preparing benzene derivatives having an isocyanatomethyl group by reacting a benzene derivative having a chloromethyl group with sodium cyanate in dimethylformamide at 60° to 160°C., in the presence of a catalytic amount of an acidic metal chloride-dimethylformamide compound, made present in the reaction mixture from the start of the reaction by being dissolved in the starting reaction mixture.

8 Claims, No Drawings

PROCESS FOR PREPARING BENZENE DERIVATIVES HAVING ISOCYANATOMETHYL GROUP

BACKGROUND OF THE INVENTION

FIELD OF THE INVENTION

This invention relates to a process for preparing isocyanic acid esters, particularly benzene derivatives having an isocyanatomethyl group.

It is a primary object of this invention to provide a process in which isocyanic acid esters having a specific structure, which are very valuable as starting materials for preparing polymer materials such as polyurethanes and polyureas, and other organic synthetic materials, can be readily prepared in large quantities without using poisonous or dangerous starting compounds such as phosgene compounds and azide compounds.

SUMMARY OF THE INVENTION

We have discovered a process whereby benzene derivatives having an isocyanatomethyl group can be obtained in an economically advantageous way and while avoiding several problems present in conventional processes for preparing such compounds, such as the use of poisonous or dangerous starting materials, as well as problems of environmental pollution and the problem of maintaining safe operating operations.

According to our invention, there is provided a process for preparing a benzene derivative having an isocyanatomethyl group, very easily and in a high yield, by reacting a benzene derivative having a chloromethyl group with sodium cyanate, in dimethylformamide, at 60° to 160°C., in the presence of a catalytic amount of an acidic metal chloride-dimethylformamide compound which is made present in the reaction mixture from the start of the reaction by being dissolved in the starting reaction mixture.

The chloromethyl group-containing benzene derivative used as a starting material in the process of this invention includes, for example, the following compounds (1) to (27) and mixtures of two or more of them. In the following formulae (1) to (27), the chloromethyl group is represented by —CH$_2$Cl and R is hydrogen or an alkyl group. Usually the alkyl group R contains from 1 to 12 carbon atoms.

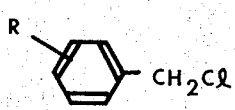  (1)

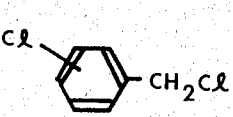  (2)

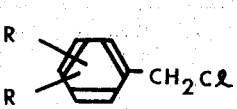  (3)

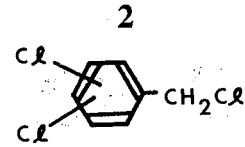  (4)

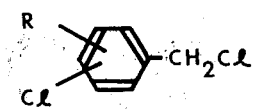  (5)

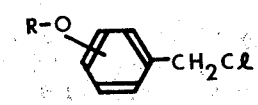  (6)

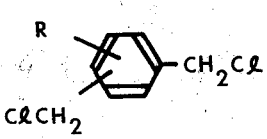  (7)

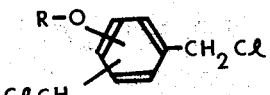  (8)

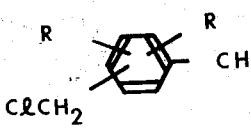  (9)

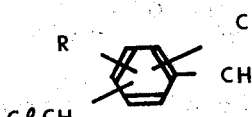  (10)

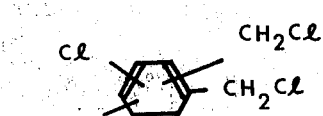  (11)

  (12)

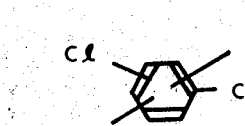  (13)

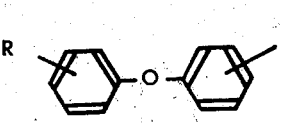  (14)

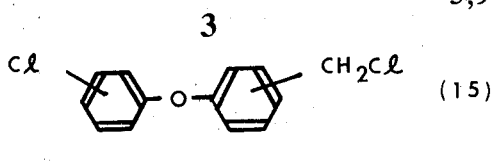
(15)

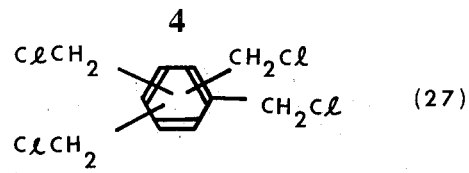
(27)

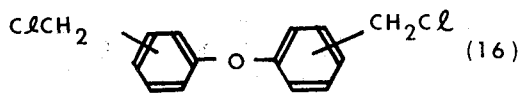
(16)

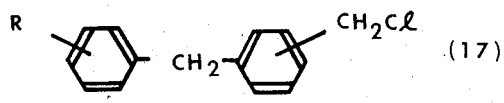
(17)

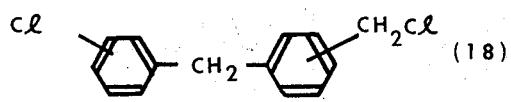
(18)

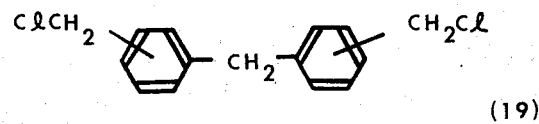
(19)

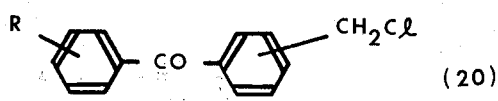
(20)

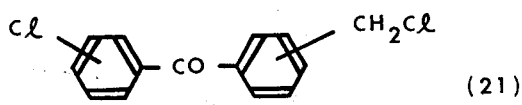
(21)

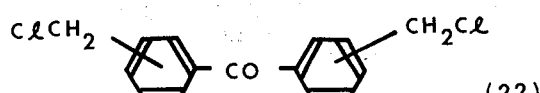
(22)

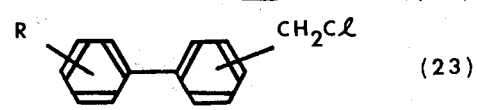
(23)

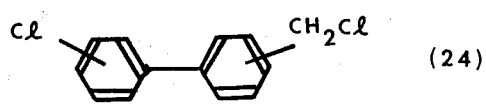
(24)

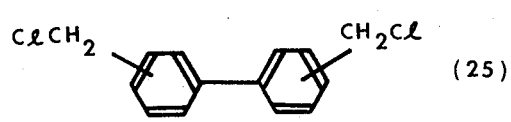
(25)

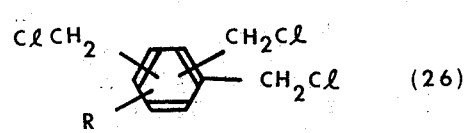
(26)

As regards the starting compounds containing one benzene nucleus, such as compounds (1) to (13), (26 and (27), compounds including three or more substituents as well as those containing one or two substituents are illustrated, but as regards compounds (14) to (25) containing two benzene nuclei, only compounds having one substituent on each benzene nucleus are shown as typical examples. However, in the case of compounds of the latter type, there are also included polysubstituted compounds corresponding to compounds (1) to (13), (26 and (27). Further, the position of each substituent is not specifically indicated as being the ortho-, meta- or para-position in formulae (1) to (27), and hence, it will readily be understood that the positions of the substituents are not critical and substitutions in any or all of these three positions are included within the scope of the invention. Isomers differing in the position of the substituent can be used singly or in the form of isomer mixtures. In principle, hereto atoms such as nitrogen, sulfur, phosphorus and metal atoms cannot be present in the substituents in the starting benzene derivative to be used in this invention, as is apparent from the foregoing formulae (1) to (27). However, in the case of bis- or poly-chloromethylated benzene derivatives, as the reaction progresses some of the chloromethyl groups are transformed to have a structure substituted with an isocyanatomethyl or isocyanuratomethyl group. Accordingly, the presence of a nitrogen atom in the substituent that can become present during the course of the reaction is exempt from the above principle. Compounds of the above formulae (1) to (27) where R is a hydrogen atom or a lower alkyl group, such as a methyl group, can readily be synthesized industrially and are known commercially available compounds. Accordingly, the names of specific compounds are not mentioned herein. These starting benzene derivatives need not be of high purity, and those of an industrial grade purity can be used as starting compounds in the process of this invention.

As the reactant sodium cyanate, there can be used in the process of this invention not only products of a reagent purity of 70 to 100 % by weight as NaOCN (that can be expressed also as NaNCO or NaCON), but also products of an industrial or herbicide grade purity. As impurities that may be contained in the sodium cyanate, there can be mentioned sodium carbonate, sodium cyanurate, urea, cyamelide, water, potassium cyanate, etc. When the total content of these impurities is lower than 30 % by weight, no particular disadvantages are brought about in the process of this invention. However, if the total content of impurities in the sodium cyanate exceeds 30 % by weight, effects that cannot be neglected are brought about owing to various side reactions, and a reduction of the yield of the intended final product occurs unless special care is taken. Accordingly, the use of sodium cyanate having more than 30 % by weight of impurities causes troubles in the practical operation of our process and hence, should be avoided. Among these impurities in sodium cyanate, water has an especially bad effect on the practice of the process of this invention. Therefore, it is recommended that the sodium cyanate be tested for water content before it is applied to the process of this invention and that sodium cyanate having a water content as low as possible be employed. It is preferred that the water content of the sodium cyanate reactant be less than 5 weight percent.

Dimethylformamide is a known compound that can be used, for example, as a spinning solvent for polyacrylonitrile, as a solvent for a gas such as acetylene or as a non-protonic polar solvent. Dimethylformamide containing 0.1 to 15 % by weight of other organic solvents such as hydrocarbons, ethers, ketones and esters can be used, provided that the water content thereof is lower than 5 % by weight, preferably lower than 2 % by weight. Thus, dimethylformamide products of any of the reagent, industrial and recovery solvent grades can be used conveniently in the process of this invention.

The term "acidic metal chloride-dimethylformamide compound", used herein, means a molecular compound or complex compound composed of a metal chloride such as mentioned below and dimethylformamide. A pure acidic metal chloride-dimethylformamide compound can be prepared by (1) a method comprising dissolving an anhydrous acidic metal chloride in dimethylformamide and concentrating the solution under an inert gas current thereby to evaporate excess dimethylformamide, or (2) by a method comprising dissolving an acidic metal chloride in dimethylformamide and adding a large quantity of a non-polar solvent to the solution to precipitate the desired compound. Most of these acidic metal chloride-dimethylformamide compounds are crystalline or powdery and are readily hydrolyzed in the presence of water. Further, they are soluble in organic solvents such as alcohols, dimethylformamide itself and esters, and they are decomposed when they are heated to a temperature higher than a specific value, which may differ for different compounds. Some of these compounds are degraded or modified by contact with moisture or with oxygen in air. Therefore, although it is not particularly required to employ such a compound having a high purity, it is advantageous to use a liquid or a solution formed by dissolving a metal chloride such as mentioned below into dimethylformamide.

As typical examples of the acidic metal chloride substance, there can be enumerated anhydrous lithium chloride, copper chloride, beryllium chloride, magnesium chloride, calcium chloride, zinc chloride, aluminum chloride silicon chloride, titanium chloride, zirconium chloride, vanadium chloride, chromium chloride and iron chloride. Further, there can be used the anhydrous oxychloride derivatives of the aforementioned metal chlorides. These anhydrous metal chlorides can be used singly or in the form of mixtures of two or more of them. Among them, lithium chloride, magnesium chloride, calcium chloride and zinc chloride are especially preferred from the industrial viewpoint. It has been found that when these metal chlorides are dissolved in water, each aqueous solution thereof has a pH lower than 7 and thus each of these metal salts is an acidic metal chloride that can be employed in this invention. Further, when these anhydrous metal chlorides are added to dimethylformamide, acidic metal chloride-dimethylformamide compounds are readily formed, in most cases with generation of heat, and the thus-formed compounds can easily be dispersed and dissolved in excess dimethylformamide and can be stored for a substantial period of time in such dispersed and dissolved state.

According to this invention, it is critical that, prior to reacting a benzene derivative having a chloromethyl group with sodium cyanate in dimethylformamide, a catalytic amount of an acidic metal chloride-dimethylformamide compound prepared from dimethylformamide and a metal chloride such as mentioned above is completely dissolved in dimethylformamide to be used as the reaction solvent and then, the reaction is initiated.

The operation of dissolving the acidic metal chloride-dimethylformamide compound completely in dimethylformamide to be used as the reaction solvent can be accomplished in practice by any of the following methods:

a. An acidic metal chloride-dimethylformamide solid compound prepared in a vessel different from the vessel to be used for the desired reaction, or a concentrated solution or suspension of such acidic metal chloride-dimethylformamide compound, in dimethylformamide, is added in a prescribed amount into the dimethylformamide to be used as the reaction solvent, and the mixture is blended, optionally under heating, to dissolve the compound sufficiently in the dimethylformamide. The thus-formed solution is used as the reaction medium.

b. A prescribed amount of an acidic metal chloride is carefully added to the dimethylformamide to be used as the solvent and the mixture is agitated to dissolve the metal chloride in dimethylformamide. In some cases, insoluble matters are formed by side reactions caused by the presence of impurities or the like. Such insoluble matters are removed by filtration. The resulting solution is stabilized and then, it is used as the reaction medium.

The acidic metal chloride-dimethylformamide compound is used in a catalytic amount. More specifically, the acidic metal chloride-dimethylformamide compound is used in an amount, calculated as the 100 % pure compound, of 0.01 to 10 mole %, preferably 0.1 to 7 mole %, based on the amount of sodium cyanate used, although this range varies to some extent depending on the purity of the sodium cyanate used. The use of such a small amount of the acidic metal chloride-dimethylformamide compound does not inhibit the reaction between the starting benzene derivative having a chloromethyl group and the sodium cyanate, in dimethylformamide, and it is very effective for improving the yield of the desired product.

The reaction between the starting benzene derivative having a chloromethyl group and sodium cyanate, in dimethylformamide, is a reaction of substitution of chlorine in the chloromethyl group by the cyanic radical, and as a result of this substitution reaction, a corresponding benzene derivative having an isocyanatomethyl group is formed, and then, some of isocyanato groups in the thus-formed product are polymerized (trimerized) to form a triazine ring. Namely, isocyanuration is effected.

It is critical that this substitution reaction is conducted at 60° to 160°C., preferably 70° to 150°C. However, it has been found that this reaction temperature is also suitable for the unwanted subsequent isocyanuration reaction. Accordingly, it is important to employ a catalyst capable of inhibiting this isocyanuration reaction. As a result of a number of experiments we have found that it is most preferred, in order to inhibit the isocyanuration reaction, that a catalytic amount of the above-mentioned acidic metal chloride-dimethylformamide compound is made present in the reaction mixture of being dissolved therein throughout the entirety of the reaction, namely, from the start of the reaction to the completion of the reaction. The purpose of this invention can be attained when this acidic metal chloride-dimethylformamide compound is used skillfully and deliberately while taking into account the reaction conditions.

The benzene derivative having an isocyanatomethyl group (end product) has a structure in which, in the chloromethyl group present in the starting material structure as shown by the foregoing formulae (1) to (27), the chlorine atom is replaced by the isocyanate group (NCO group). In some cases, benzene derivatives having some of such isocyanate groups trimerized to form an isocyanurate group are included in the above benzene derivative having an isocyanatomethyl group (end product). However, in such benzene derivatives having an isocyanurate group in addition to the isocyanatomethyl group it is indispensible that a considerable amount of the isocyanatomethyl group should be contained in the molecule.

Whether the isocyanatomethyl group-containing benzene derivative obtained according to the process of this invention is an isocyanate (an isocyanic acid ester) or an isocyanatoisocyanurate (an isocyanic-isocyanuric acid ester), or a mixture of both, is influenced by the foregoing reaction conditions, the kind and amount of the catalyst used and the amount, kind and properties of the starting derivative having a chloromethyl group.

In the process of this invention, it is generally preferred that the sodium cyanate is used in an amount of 0.9 to 1.6 moles per mole of chloromethyl group in the starting chloromethyl group-containing benzene derivative although the amount of sodium cyanate used varies to some extent depending on the purity thereof. It is also preferred that dimethylformamide, employed as the solvent, is used in an amount of about 1 to 10 moles of the chloromethyl group-containing benzene derivative. The amounts used of the chloromethyl group-containing benzene derivative, sodium cyanate and dimethylformamide as the solvent are so choosen that the foregoing requirements are satisfied.

The process of this invention can be practiced either batchwise or continuously. The starting compounds and solvent (inclusive of the catalyst) should be mixed by a procedure suitable for the particular reaction apparatus used. Further, separation of the end product from the reaction mixture can be preformed by a variety of optional methods suitable for the specific type of separation apparatus used.

Some typical experiments will now be given as Examples illustrative of this invention. Accordingly, it will readily be understood that the scope of this invention is not limited by these Examples.

EXAMPLE 1

In order to examine the effect of the acidic metal chloride-dimethylformamide compound on the reaction between benzyl chloride and sodium cyanate, in dimethylformamide, the relative reaction velocity was determined by performing experiments using a considerable amount of dimethylformamide.

708 Moles of dimethylformamide (having a purity of 100%) 0.45 mole of benzyl chloride and 0.45 mole of sodium cyanate (having a purity of 100) were charged into each of two flasks. In one of these two flasks, 0.02 mole of calcium chloride (having a purity of 100%) was added in advance to the dimethylformamide to form a dimethylformamide solution of a calcium chloride-dimethylformamide compound effective as a catalyst. Both the flasks were maintained at 80°C. and sampling was conducted at intervals of 30 minutes for analysis of the reaction mixture. The conversion of benzyl chloride to benzyl isocyanate was determined to obtain a second-order velocity constant K (l/mole.sec) of the substitution reaction. As a result, it was found that the velocity constant K was 0.0121 when no catalyst was added and the velocity constant K was 0.0106 when catalyst was added. From these values, it is seen that the calcium chloride-dimethylformamide compound acts as a negative catalyst in the substitution reaction. When the reaction mixture was analyzed to determine the third-order velocity constant k ($l^2$/$mole^2$.sec) of the formation of tribenzyl isocyanurate, it was found that the $k$ value was 0.0045 when no catalyst was added and the $k$ value was 0.0020 when catalyst was added. From the foregoing experimental results, it will be readily understood that when a catalytic amount of the calcium chloride-dimethylformamide compound is made present in the reaction mixture, a longer time is required for completion of the substitution reaction for forming benzyl isocyanate from benzyl chloride, but if the reaction is conducted for a sufficient period of time, the trimerization reaction for forming tribenzyl isocyanurate is highly inhibited and hence, the yield of benzyl isocyanate is improved.

EXAMPLE 2

100 g of anhydrous calcium chloride powder was added to 100 g of dimethylformamide with agitation, and the mixture was heated to form a paste. The paste was evaporated to dryness under a reduced pressure and below 50°C. to obtain a coarse white crystalline powder. Analysis showed that the powder was a calcium chloride-dimethylformamide compound. 20 g of this white crystalline powder was dissolved in 300 g of dimethylformamide, and 126.6 g of benzyl chloride was added to the solution and 75 g of sodium cyanate powder (having a purity of 98 %) was added to the solution with agitation, at an elevated temperature of 100°C., over a period of 4 hours. When 5 hours had passed from the start of the reaction, the reaction mixtures was treated under reduced pressure to recover dimethylformamide by distillation, and the residue was extracted with benzene and the benzene extract was distilled under reduced pressure to obtain 113 g of benzyl isocyanate (the yield being about 85 %). When the above reaction was repeated without adding 20 g of the white crystalline powder, tribenzyl isocyanurate was obtained in a yield of about 70 %, instead of benzyl isocyanate.

EXAMPLE 3

Reactions were conducted in the same manner described in Example 2 except that 20 g of various acidic metal chloride-dimethylformamide compounds, as shown in Table 1, which were prepared in the same manner as the calcium chloride-dimethylformamide compound used in Example 2, were used instead of the calcium chloride-dimethylformamide compound. Benzyl isocyanate was obtained in the yields shown in Table 1.

Table 1

| Chemical Formula of Acidic Metal Chloride-Dimethylformamide Compound | Yield (%) of Benzyl Isocyanate |
|---|---|
| $LiCl\cdot HCON(CH_3)_2$ | 82 |
| $CuCl_2\cdot HCON(CH_3)_2$ | 87 |
| $BeCl_2\cdot HCON(CH_3)_2$ | 88 |
| $MgCl_2\cdot HCON(CH_3)_2$ | 85 |
| $ZnCl_2\cdot HCON(CH_3)_2$ | 85 |
| $AlCl_3\cdot HCON(CH_3)_2$ | 80 |
| $TiCl_4\cdot HCON(CH_3)_2$ | 76 |
| $TiCl_2\cdot HCON(CH_3)_2$ | 78 |
| $ZrCl_4\cdot HCON(CH_3)_2$ | 82 |
| $VOCl_3\cdot HCON(CH_3)_2$ | 88 |
| $FeCl_3\cdot HCON(CH_3)_2$ | 82 |

EXAMPLE 4

The reaction was conducted in the same manner as described in Example 2 except that 1 mole of the various starting compounds shown in Table 2 were used instead of benzyl chloride. The products obtained and their yields are shown in Table 2. Among the products shown in Table 2, those containing two benzene nuclei were purified by the recrystallization method.

Table 2

| Chemical Formula of Starting Compound | Chemical Formula of Product | Yield (%) of Product |
|---|---|---|
| $CH_3\text{-}C_6H_4\text{-}CH_2Cl$ (para) | $CH_3\text{-}C_6H_4\text{-}CH_2NCO$ (para) | 89 |
| $o\text{-}CH_3\text{-}C_6H_4\text{-}CH_2Cl$ | $o\text{-}CH_3\text{-}C_6H_4\text{-}CH_2NCO$ | 82 |
| $2,4\text{-}(CH_3)_2\text{-}C_6H_3\text{-}CH_2Cl$ | $2,4\text{-}(CH_3)_2\text{-}C_6H_3\text{-}CH_2NCO$ | 75 |
| $Cl\text{-}C_6H_4\text{-}CH_2Cl$ | $Cl\text{-}C_6H_4\text{-}CH_2NCO$ | 90 |
| $CH_3O\text{-}C_6H_4\text{-}CH_2Cl$ | $CH_3O\text{-}C_6H_4\text{-}CH_2NCO$ | 77 |
| $C_6H_5\text{-}O\text{-}C_6H_4\text{-}CH_2Cl$ | $C_6H_5\text{-}O\text{-}C_6H_4\text{-}CH_2NCO$ | 62 |
| $CH_3\text{-}C_6H_4\text{-}O\text{-}C_6H_4\text{-}CH_2Cl$ | $CH_3\text{-}C_6H_4\text{-}O\text{-}C_6H_4\text{-}CH_2NCO$ | 71 |
| $Cl\text{-}C_6H_4\text{-}O\text{-}C_6H_4\text{-}CH_2Cl$ | $Cl\text{-}C_6H_4\text{-}O\text{-}C_6H_4\text{-}CH_2NCO$ | 70 |
| $C_6H_5\text{-}CO\text{-}C_6H_4\text{-}CH_2Cl$ | $C_6H_5\text{-}CO\text{-}C_6H_4\text{-}CH_2NCO$ | 69 |
| $C_6H_5\text{-}C_6H_4\text{-}CH_2Cl$ | $C_6H_5\text{-}C_6H_4\text{-}CH_2NCO$ | 80 |
| $Cl\text{-}C_6H_4\text{-}C_6H_4\text{-}CH_2Cl$ | $Cl\text{-}C_6H_4\text{-}C_6H_4\text{-}CH_2NCO$ | 82 |

EXAMPLE 5

90 g of anhydrous 6, chloride was dissolved in 200 ml of dimethylformamide, and dimethylformamide was distilled off under reduced pressure on a warm water bath to obtain a magnesium chloride-dimethylformamide compound in the form of a white crystalline powder. 30 g of the thus-formed magnesium chloride-dimethylformamide compound was dissolved in 700 ml of dimethylformamide, and the solution was mixed with 150 g of sodium cyanate (having a purity of 90 %), 1 mole of a starting bischloromethyl compound indicated in Table 3 and 0.5 g of potassium iodide (or 0.7 g of potassium bromide) as the reaction promotor. The reaction was conducted at 90° C. for 3 hours under vigorous agitation, and then 300 ml of ligroin was added to the reaction mixture and it was cooled. Then, the precipitated inorganic salt was separated by filtration and the separated inorganic salt was washed with 100 ml of ligroin. The washing liquid was combined with the filtrate and the mixture was subjected to distillation to recover ligroin and dimethylformamide. Then, the distillation residue was extracted with cold benzene to separate the residue into an insoluble portion and a soluble portion. The majority of the benzene was distilled from the benzene extract, and the residual liquid was cooled, mixed with ligroin and recrystallized from a liquid mixture of benzene and ligroin to obtain a product shown in Table 3 in the yield also shown in Table 3. In this synthesis method, the material that could not be extracted with benzene was composed mainly of polyisocyanatepolyisocyanurate. It was found that the yield of this product could be increased by reducing the amount used of the magnesium chloride-dimethylformamide compound. It was also found, however, that if the magnesium chloride-dimethylformamide was not added at all, gelation occurred in the reaction mixture as the reaction progressed, especially at high temperatures exceeding 110°C., and neither an isocyanic acid ester nor an isocyanuric acid ester was obtained, but only a polyisocyanurate having a very high molecular weight was obtained. In this Example, dimethylformamide and ligroin were recovered in very dry condition and they could be used repeatedly for the synthesis reaction.

Table 3

| Chemical Formula of Starting Compound | Chemical Formula of Product | Yield (%) of Product |
|---|---|---|
| ClCH₂–C₆H₄–CH₂Cl | OCNCH₂–C₆H₄–CH₂NCO | 82 |
| ClCH₂–C₆H₄–CH₂Cl (meta) | OCNCH₂–C₆H₄–CH₂NCO (meta) | 80 |
| ClCH₂–C₆H₃(CH₃)–CH₂Cl | OCNCH₂–C₆H₃(CH₃)–CH₂NCO | 78 |
| ClCH₂–C₆H₃(Cl)–CH₂Cl | OCNCH₂–C₆H₃(Cl)–CH₂NCO | 69 |
| CH₃O–C₆H₃(CH₂Cl)–CH₂Cl | CH₃O–C₆H₃(CH₂NCO)–CH₂NCO | 75 |
| ClCH₂–C₆H₄–O–C₆H₄–CH₂Cl | OCNCH₂–C₆H₄–O–C₆H₄–CH₂NCO | 82 |
| ClCH₂–C₆H₄–CO–C₆H₄–CH₂Cl | OCNCH₂–C₆H₄–CO–C₆H₄–CH₂NCO | 80 |
| ClCH₂–C₆H₄–C₆H₄–CH₂Cl | OCNCH₂–C₆H₄–C₆H₄–CH₂NCO | 77 |
| ClCH₂–C₆H₂(Cl)(Cl)–C₆H₂(Cl)(Cl)–CH₂Cl | OCNCH₂–C₆H₂(Cl)(Cl)–C₆H₂(Cl)(Cl)–CH₂NCO | 86 |

EXAMPLE 6

The reaction was conducted in the same manner as described in Example 5 by employing as the starting material 1 mole of a mixture of xylene isomers having a dichlorinated side chain (mixture of xylene dichloride isomers). As a result, a semi-solid mixture of xylylene diisocyanate isomers was obtained in a yield of 81 %. In this case, if the amount of the magnesium chloride-dimethylformamide was reduced to 10 g. an isocyanurate-polyisocyanate having the following formula and a xylylylene diisocyanate isomer mixture were obtained as the reaction product in yields of about 60 % and about 20 %, respectively. The thus-obtained product composed of the xylylene diisocyanate and isocyanurate-polyisocyanate could be used as the starting substance for synthesis of polyurea isocyanate in the asprepared state without separation or purification. Synthetic resins prepared from such product were found to have excellent heat resistance, flame retardancy, water resistance and chemical resistance.

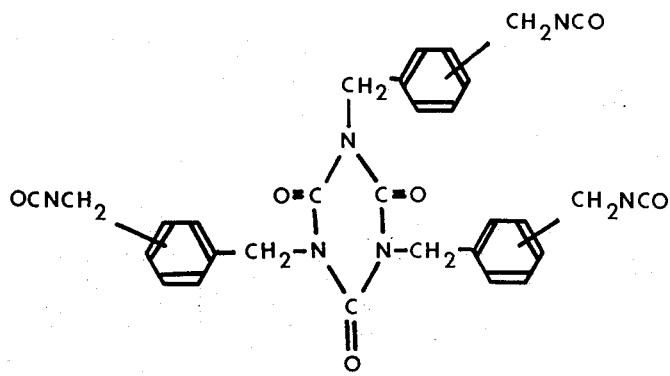

The embodiments of the invention in which an exclusive property or privilege is claimed are defined as follows:

1. A process for preparing benzene derivatives having one or more isocyanatomethyl side chains, comprising the steps of:
    adding to liquid dimethylformamide having completely dissolved therein a catalytic amount of acidic metal chloride-dimethylformamide compound in which said acidic metal chloride moiety is selected from the group consisting of lithium chloride, copper chloride, beryllium chloride, magnesium chloride, calcium chloride, zinc chloride, aluminum chloride, silicon chloride, titanium chloride, zirconium chloride, vanadium chloride, chromium chloride, iron chloride, their corresponding oxychlorides and mixtures thereof, reactants consisting essentially of
    1. a benzene derivative selected from the group consisting of chloromethylbenzene, bis-chloromethylbenzene, tris-chloromethylbenzene and nucleus-substituted derivatives thereof wherein the substituents are free of atoms of elements other than hydrogen, carbon, chlorine and oxygen, and
    2. sodium cyanate having a purity of at least 70 weight percent,
    and reacting the resulting mixture at a temperature of 60° to 160°C. until there is formed the corresponding benzene derivative having one or more isocyanatomethyl side chains, and recovering the latter benzene derivative from the reaction mixture.

2. A process according to claim 1, in which the dimethylformamide contains from 0 to 15 weight percent of organic solvents and 0 to 5 weight percent of water.

3. A process according to claim 1, in which said acidic metal chloride-dimethylformamide compound is prepared by reacting anhydrous acidic metal chloride with dimethylformamide.

4. A process according to claim 3, in which said acidic metal chloride forms a solution having a pH lower than 7 when dissolved in water.

5. A process according to claim 3, in which the amount of said acidic metal chloride-dimethylformamide compound is from 0.01 to 10 mole percent, based on the amount of sodium cyanate, both calculated on the 100 % purity basis.

6. A process according to claim 1, in which the amount of reactant (2) is from 0.9 to 1.6 moles, per mole of chloromethyl groups of reactant (1), both calculated on a 100 % purity basis.

7. A process according to claim 7, in which the amount of liquid dimethylformamide is from 1 to 10 moles, per mole of reactant (1).

8. A process according to claim 1 in which said acidic metal chloride is selected from the group consisting of lithium chloride, magnesium chloride, calcium chloride and zinc chloride.

* * * * *

UNITED STATES PATENT AND TRADEMARK OFFICE
CERTIFICATE OF CORRECTION

PATENT NO. : 3 948 966
DATED : April 6, 1976
INVENTOR(S) : Yoshiaki Inamoto et al It is certified that error appears in the above—identified patent and that said Letters Patent are hereby corrected as shown below:

Column 14, line 23; change "Claim 7" to ---Claim 6---.

Signed and Sealed this

Twenty-seventh Day of July 1976

[SEAL]

Attest:

RUTH C. MASON
Attesting Officer

C. MARSHALL DANN
Commissioner of Patents and Trademarks